United States Patent
Tsuji et al.

(10) Patent No.: US 6,639,085 B2
(45) Date of Patent: Oct. 28, 2003

(54) PROCESS FOR PRODUCING PROPYLENE OXIDE

(75) Inventors: Junpei Tsuji, Ichihara (JP); Jun Yamamoto, Sodegaura (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/221,357

(22) PCT Filed: Mar. 19, 2001

(86) PCT No.: PCT/JP01/02186
§ 371 (c)(1),
(2), (4) Date: Sep. 12, 2002

(87) PCT Pub. No.: WO01/70710
PCT Pub. Date: Sep. 27, 2001

(65) Prior Publication Data
US 2003/0032823 A1 Feb. 13, 2003

(30) Foreign Application Priority Data
Mar. 24, 2000 (JP) .......................................... 2000-83961

(51) Int. Cl.⁷ .............................................. C07D 301/19
(52) U.S. Cl. ...................................................... 549/521
(58) Field of Search ........................................ 549/529

(56) References Cited

U.S. PATENT DOCUMENTS

| | | | |
|---|---|---|---|
| 3,350,422 A | 10/1967 | Kollar | |
| 5,723,637 A | 3/1998 | Tsuji et al. | |

FOREIGN PATENT DOCUMENTS

WO   WO 0170711   * 9/2001

OTHER PUBLICATIONS

Mistrik et al., CAS:77:5311, 1972, "Olefin oxides by epoxidation of olefins with aromatic hydroperoxides".*
Lewandowski et al., CAS:134:133268, 2000, "Integrated manufacture of propylene oxide, phenol, and acetone".*
Aldrich catalog, 1990–1991, p. 355 and 1104.*
Mistrik et al., CAS:77:5311, 1972, "Olefin oxides by epoxidation of olefins with aromatic hydroperoxides".*
Lewandowski et al., CAS:134:133268, 2000, "Integrated manufacture of propylene oxide, phenol, and acetone".*

* cited by examiner

Primary Examiner—Joseph K. McKane
Assistant Examiner—Rei Tsang Shiao
(74) Attorney, Agent, or Firm—Sughrue Mion, PLLC

(57) ABSTRACT

A process for producing propylene oxide, which comprises steps described below, wherein the concentration of water in a solution containing isopropylbenzene hydroperoxide to be supplied to the epoxidation step is 1% by weight or less:

oxidation step; a step in which isopropylbenzene is oxidized to obtain isopropylbenzene hydroperoxide, epoxidation step; a step in which isopropylbenzene hydroperoxide obtained in the oxidation step is reacted with propylene to obtain propylene oxide and cumyl alcohol, and hydrogenolysis step; a step in which cumyl alcohol obtained in the epoxidation step is subjected to hydrogenolysis to obtain isopropylbenzene, and said isopropylbenzene is recycled to the oxidation step as a raw material for the oxidation step.

6 Claims, No Drawings

PROCESS FOR PRODUCING PROPYLENE OXIDE

This application is a 371 of PCT/JP01/02186, filed on Mar. 19, 2001.

TECHNICAL FIELD

The present invention relates to a process for producing propylene oxide. More particularly, the invention relates to a process for producing propylene oxide, wherein said process for producing propylene oxide has excellent characteristics that propylene is converted to propylene oxide using isopropylbenzene hydroperoxide obtained from isopropylbenzene, as an oxygen carrier, that said isopropylbenzene can be repeatedly used, that the epoxidation for obtaining propylene oxide from propylene, can be conducted under a high yield, and that the load in a purification step of propylene oxide as a product can be reduced.

BACKGROUND ART

A process in which propylene is oxidized using ethylbenzene hydroperoxide as an oxygen carrier to give propylene oxide and styrene is known as Halcon process. Since, in this process, styrene is inevitably produced together with propylene oxide, it is unsatisfactory from the viewpoint that only propylene oxide is to be selectively produced.

On the other hand, a concept of a process in which propylene is converted to propylene oxide using isopropylbenzene hydroperoxide obtained from isopropylbenzene, as an oxygen carrier, and said isopropylbenzene is repeatedly used, is described in Czechoslovak Patent No. CS 140,743. The process described in said patent does not contain precise descriptions on necessary steps except oxidation step, epoxidation step and hydrogenolysis step. Various problems arise in practical recycling of isopropylbenzene and therefore the patent cannot be said as sufficient for industrial realization.

DISCLOSURE OF THE INVENTION

Under such circumstances, an object of the present invention is to provide a process for producing propylene oxide, wherein said process for producing propylene oxide has excellent characteristics that propylene is converted to propylene oxide using isopropylbenzene hydroperoxide obtained from isopropylbenzene, as an oxygen carrier, that said isopropylbenzene can be repeatedly used, that the epoxidation for obtaining propylene oxide from propylene can be conducted under a high yield, and that the load in a purification step of propylene oxide as a product can be reduced.

Namely, the invention relates to a process for producing propylene oxide, which comprises steps described below, wherein the concentration of water in a solution containing isopropylbenzene hydroperoxide to be supplied to the epoxidation step is 1% by weight or less:

oxidation step; a step in which isopropylbenzene is oxidized to obtain isopropylbenzene hydroperoxide, epoxidation step; a step in which isopropylbenzene hydroperoxide obtained in the oxidation step is reacted with propylene to obtain propylene oxide and cumyl alcohol, and hydrogenolysis step; a step in which cumyl alcohol obtained in the epoxidation step is subjected to hydrogenolysis to obtain isopropylbenzene, and said isopropylbenzene is recycled to the oxidation step as a raw material for the oxidation step.

BEST MODE FOR CARRYING OUT THE INVENTION

The oxidation step in the present invention is a step in which isopropylbenzene is oxidized to obtain isopropylbenzene hydroperoxide. The oxidation of isopropylbenzene is usually effected by autoxidation with oxygen-containing gas such as the air, an oxygen-enriched air or the like. The oxidation reaction may be carried out without any additive or with an additive such as an alkali. The reaction temperature is usually 50 to 200° C., and the reaction pressure is usually between the atmospheric pressure and 5 MPa. In the oxidation with an additive, the alkali includes alkali metal compounds such as NaOH, KOH and aqueous solutions thereof; and alkaline earth metal compounds, alkali metal carbonates such as $Na_2CO_3$, $NaHCO_3$, ammonia, $(NH_4)_2CO_3$, alkali metal ammonium carbonates and the like, and aqueous solution thereof.

The epoxidation step in the present invention is a step in which isopropylbenzene hydroperoxide obtained in the oxidation step is reacted with propylene to obtain propylene oxide and cumyl alcohol. From a viewpoint that the desired product should be obtained in a high yield and under a high selectivity, the epoxidation step is preferably conducted in the presence of a catalyst containing a titanium-containing silicon oxide. The catalyst is preferably a catalyst containing titanium chemically bound to silicon oxide, so-called titanium-silica catalyst. Examples may include products in which a titanium compound is supported on a silica carrier, products in which a titanium compound is compounded with a silicon oxide by a co-precipitation or sol-gel method, titanium-containing zeolite compounds or the like.

In the present invention, isopropylbenzene hydroperoxide used as the raw material for the epoxidation step may be a dilute or thick purification or non-purification product.

The epoxidation reaction is carried out by contacting propylene and isopropylbenzene hydroperoxide with a catalyst. The reaction may be conducted in a liquid phase using a solvent. The solvent must be a liquid under the reaction temperature and pressure, and substantially inert to the reactants and the product. The solvent may be composed of a substance existing in a solution of the hydroperoxide used. When, for example, isopropylbenzene hydroperoxide is a mixture with isopropylbenzene as the raw material, it is also possible to use said material, without adding a solvent in particular, as the solvent. Other useful solvents include aromatic single-ring compounds (for example, benzene, toluene, chlorobenzene and o-dichlorobenzene), alkane (for example, octane, decane and dodecane) and the like.

The epoxidation temperature is generally 0 to 200° C. and preferably 25 to 200° C. The pressure may be any pressure sufficient to keep liquid state of the reaction mixture. Generally, the pressure is advantageously 100 to 10,000 kPa.

The epoxidation can advantageously be carried out with a catalyst in the form of a slurry or a fixed-bed. The fixed-bed is preferred in the case of a large-scale industrial operation. In addition, the reaction can be carried out by a batch process, a semi-continuous process, a continuous process or the like. When a liquid containing the raw materials for reaction is passed through a fixed-bed, the catalyst is not contained at all or substantially in a liquid mixture discharged from a reaction zone.

The hydrogenolysis step in the present invention is a step in which cumyl alcohol obtained in the epoxidation step is subjected to hydrogenolysis to obtain isopropylbenzene, and said isopropylbenzene is recycled to the oxidation step as the raw material for the oxidation step. In other words, the same product, i.e. isopropylbenzene, used in the oxidation step is recovered. The hydrogenolysis is usually carried out by contacting cumyl alcohol and hydrogen with a catalyst.

As a catalyst, any catalyst having a hydrogenation ability can be used. Examples of the catalyst include metal catalysts of metals of the group 8th to 10th such as those of cobalt, nickel, palladium and the like and metal catalysts of metals of the group 11th or 12th metals such as those of copper, zinc and the like. Copper catalysts are preferred from the viewpoint that by-products are suppressed. The copper catalysts include copper, Raney copper, copper-chromium, copper-zinc, copper-chromium-zinc, copper-silica, copper-alumina and the like. The reaction can be conducted in a liquid phase using a solvent or in a gaseous phase. The solvent must be substantially inert to the reactants and the product. The solvent may contain a substance existing in a solution of the cumyl alcohol used. When, for example, cumyl alcohol is a mixture with isopropylbenzene as the product, it is possible to use this, without adding a solvent in particular, as the solvent.

Other useful solvents include alkane (for example, octane, decane and dodecane), aromatic single-ring compounds (for example, benzene, ethylbenzene and toluene), and others. The temperature for the hydrogenolysis reaction is generally 0 to 500° C. and preferably 30 to 400° C. Generally, the pressure is advantageously 100 to 10,000 kPa. The hydrogenolysis can advantageously be carried out with a catalyst in the form of a slurry or a fixed-bed.

The process of the present invention can be carried out by a batch process, a semi-continuous process or a continuous process. When a solution or a gas containing the raw materials for reaction is passed through a fixed-bed, the catalyst is not contained at all or substantially in a liquid mixture discharged from the reaction zone.

In the present invention, it is necessary that the concentration of water in a solution containing isopropylbenzene hydroperoxide to be supplied to the epoxidation step is controlled to 1% by weight or less, preferably 0.5% by weight or less. Water is reacted with propylene oxide in the epoxidation step to form glycols, and therefore, decreases a yield of propylene oxide. Besides, propylene oxide is separated from the reaction liquid.

But, since water in the reaction liquid is separated to propylene oxide side, an extra energy is required further to separate propylene oxide and water.

From these view points, it is necessary to control the concentration of water in the solution containing isopropylbenzene hydroperoxide to be supplied to the epoxidation step within the range of the present invention.

As a method of controlling the water concentration, any method of a method of removing all or part of water to outside of the system of the steps in the present invention by distillation, extraction or the like; a method of converting to another compound by a reaction; a method of reducing the concentration by absorption or the like; and the like, may be used.

When removing to outside of the system, a step of removal of water (herein-after, may be referred to as "water removing step") can be conducted in at least one place in the oxidation step, epoxidation step and hydrogenolysis step or in at least one place between which the steps are connected. And, taking into consideration that water is produced in the oxidation step, there are cases of adding water in the oxidation step and of operation of water washing after the oxidation step, the water removal before the epoxidation step is preferable from the view point of effective batch removal.

Further, in the present invention, the concentration of an organic acid of the solution containing isopropylbenzene hydroperoxide to be supplied to the epoxidation step is preferably 0.5% by weight or less, more preferably 0.1% by weight or less.

By specifying within this range, the activity of the catalyst used in the epoxidation step can be maintained at a high level and the life of the catalyst can be kept for longer time.

Still further, in the present invention, it is preferable that isopropylbenzene hydroperoxide supplied to an epoxidation step has not undergone a heat history including heating at a temperature not lower than the temperature (t ° C.) represented by the following equation(1), $$t(°C.)=150-0.8 \times W \tag{1}$$

W: content (% by weight) of isopropylbenzene hydroperoxide in a solution containing isopropylbenzene hydroperoxide.

By specifying within this range, the activity of the catalyst used in the epoxidation step can be maintained at high level and the life of the catalyst can be kept for longer time.

Moreover, in the present invention, the concentration of sodium of the solution containing isopropylbenzene hydroperoxide to be supplied to the epoxidation step is preferably 0.1% by weight or less.

By specifying within this range, the activity of the catalyst used in the epoxidation step can be maintained at high level and the life of the catalyst can be kept for longer time.

EXAMPLE 1

A solution containing isopropylbenzene hydroperoxide having a water concentration of 0.2% by weight is continuously passed through a fixed bed flowing reactor in the presence of a titanium-containing silicon oxide catalyst at a rate of 10 times by mol of propylene per 1 mol of isopropylbenzene hydroperoxide. The conversion of cumene hydroperoxide is kept 99% and the reaction is steadily stabilized by controlling the inlet temperature. At this case, the reaction temperature is 60° C., and the selectivity of propylene oxide is 95.0%.

Comparative Example 1

When the epoxidation is carried out in the same manner as in Example 1 except that the water concentration is 2% by weight, the selectivity of propylene oxide decreases 91.4%. When propylene oxide is separated from the reaction liquid after the epoxidation, an extra energy for separation step of propylene oxide is required because water in the reaction liquid is separated propylene oxide side.

Industrial Applicability

As described above, according to the present invention, there can be provided a process for producing propylene oxide, wherein said process for producing propylene oxide has excellent characteristics that propylene is converted to propylene oxide using isopropylbenzene hydroperoxide obtained from isopropylbenzene, as an oxygen carrier, that said isopropylbenzene can be repeatedly used, that the epoxidation can be conducted under a high yield, and that the load in a purification step of propylene oxide as a product can be reduced.

What is claimed is:

1. A process for producing propylene oxide in a reaction system, which comprises the following steps:

oxidation step; a step in which isopropylbenzene is oxidized to obtain isopropylbenzene hydroperoxide, epoxidation step; a step in which isopropylbenzene hydroperoxide obtained in the oxidation step is reacted with propylene to obtain propylene oxide and cumyl alcohol, hydrogenolysis step; a step in which cumyl alcohol obtained in the epoxidation step is subjected to hydrogenolysis to obtain isopropylbenzene, and said isopropylbenzene is recycled to the oxidation step as a raw material for the oxidation step, and a step for removing water to outside of the reaction system so that the concentration of water in a solution containing isopropylbenzene hydroperoxide to be supplied to the epoxidation step is 1% by weight or less.

2. The process according to claim 1, wherein the concentration of water in the solution of isopropylbenzene hydroperoxide is 0.5% by weight or less.

3. The process according to claim 1, wherein the concentration of water in the solution of isopropylbenzene hydroperoxide is 0.1% by weight or less.

4. The process according to claim 1, wherein the step for removing water to outside of the reaction system is between the oxidation step and epoxidation step.

5. The process according to claim 2, wherein the step for removing water to outside of the reaction system is between the oxidation step and epoxidation step.

6. The process according to claim 3, wherein the step for removing water to outside of the reaction system is between the oxidation step and epoxidation step.

* * * * *